United States Patent [19]

Cohen

[11] Patent Number: 4,785,815
[45] Date of Patent: Nov. 22, 1988

[54] APPARATUS FOR LOCATING AND ABLATING CARDIAC CONDUCTION PATHWAYS

[75] Inventor: Donald Cohen, Miami, Fla.

[73] Assignee: Cordis Corporation, Miami, Fla.

[21] Appl. No.: 790,315

[22] Filed: Oct. 23, 1985

[51] Int. Cl.[4] .......................... A61B 5/04; A61N 5/00
[52] U.S. Cl. .................................. 128/642; 129/303.1
[58] Field of Search ................. 128/303.1, 395–398, 128/642

[56] References Cited

U.S. PATENT DOCUMENTS

| 4,172,451 | 10/1979 | Kline | 128/642 |
| 4,445,892 | 5/1984 | Hussein et al. | 604/101 |
| 4,576,177 | 3/1986 | Webster, Jr. | 128/303.1 X |

FOREIGN PATENT DOCUMENTS

| 2560052 | 8/1985 | France | 128/785 |
| 1140792 | 2/1985 | U.S.S.R. | 128/786 |

OTHER PUBLICATIONS

Tripolar HIS-Bundle Electrode, USCI Corp., 10/1971.
Gillette, "Catheter Ablation . . . ", Cardio, Mar. 1984, pp. 67–69.
Morady et al, "Transvenous Catheter Ablation . . . ", N.E. J Med. Mar. 1984, vol. 310, No. 11, pp. 705–707.
Lee et al, "Effects of Laser Irradiation Delivered . . . Myocardima", Am. Heart Journal, Sep. 1983, pp. 587–590.

*Primary Examiner*—Lee S. Cohen
*Attorney, Agent, or Firm*—Tarolli, Sundheim & Covell

[57] ABSTRACT

Apparatus for locating and ablating cardiac conduction pathways is provided herein. This includes a catheter tube which carries, at its distal end, at least one electrode for sensing membrane potentials within a heart. The catheter also carries a device for ablating at least a portion of the thus located pathway.

24 Claims, 3 Drawing Sheets

APPARATUS FOR LOCATING AND ABLATING CARDIAC CONDUCTION PATHWAYS

BACKGROUND OF THE INVENTION

This invention relates to the art of catheters and more particularly to a catheter having means for locating and then ablating cardiac conduction pathways.

The heart, in a human, is a four chamber muscular organ that pumps blood through various conduits to and from all parts of the body. In order that blood be moved in the cardiovascular system in an orderly manner, it is necessary that the heart muscles contract and relax in an orderly sequence so that the valves of the system open and close at proper times during the cycle. The control is initiated by a special structure known as a sino-atrial node (SA node). This is the natural pacemaker of the heart and is specialized tissue located within the muscle walls of the right atrium. Basically, the SA node provides what may be considered dominance over the inherent or natural rhythmic contractions of the atria and ventricles. This dominance is transmitted by ionic impulses through cardiac conduction pathways in the atria and the ventricles thereby causing the heart to contract and relax in an orderly sequence at a rate dictated by the SA node. The sequence insures that each ventricular contraction maximizes the volume of blood flowing to the pulmonary and systemic circulation. The SA node has an inherent rate or rhythm which can be modified by the action of the sympathetic and parasympathetic nervous system.

The impulses are transmitted from the SA node through the atria to the atrio-ventricular node (A-V node) and, thence, to the ventricles by way of cardiac conduction pathways (Bundle of His and Purkinje fibers). The A-V node transmits the impulses by way of a common pathway, also known as the Bundle of His and, thence, by way of two lower branches to a network of fibers which cover the inside of each ventricle. This conductive network extends to the outer covering of the heart and is called the Purkinje system. The ionic or current flow in the cardiac conduction pathways may be interrupted or altered by disease which can cause the formation of scar tissue. When injury occurs in the cardiac conductive pathways or to the microcardium, the electrical impulses as dictated by the SA node are not transmitted normally, then rythmic disturbances can take place in the heart which are called cardiac arhythmias (dysrhymthmias). A principle means used by physicians for analysis of cardiac dysrhythmias is the electro-cardiogram.

The term bradycardia is used to describe an abnormal slowing of the cardiac contractions. Tachycardia is a term used to describe excessive rapidity of heart action. Tachycardia dysrhythmia or tachydysrhythmia may impose substantial risk to a patient because diseased hearts cannot usually tolerate such rapid rates for extensive periods. Thus, when there is a marked underlying heart disease, such rapid rates may cause hypotension and heart failure. Tachycardia in those patients with underlying cardiac disease can degenerate into a more serious ventricular dysrhythmia such as fibrillation.

It is therefore desirable in situations of abnormal tachycardia, resistant to medical management, to terminate this rapid rate by ablating at least a portion of the cardiac conduction pathway either to decrease the heart rate or to disrupt the orderly sequence partially or totally.

If the origin of the tachycardia is above the ventricles it is termed Supra Ventricular Tachycardia (SVT). SVT is only life threatening if the atrial rate is exceedingly high and the atrial activity is conducted to the ventricles in a 1:1 ratio. If during an episode of SVT the ventricular rate was ½ of the atrial rate, there would be no threat to survival. Thus, it may be desirable to create (via ablation) second degree heart block (wherein the ventricular rate is related to the atrial, but only 1 in every n beats are conducted). For example, if the atrial rate was 250 b.p.m. (beats per minute), the ventricular rate would be a safe 125 b.p.m. if there were chronic 2:1 second degree block. A drawback of this is that at rest the ventricular rate may be dangerously slow in the absence of an artificial pacemaker. Thus, a more desirable state may be to ablate sufficient tissue to cause only first degree heart block at rest. This implies slowed conduction through the AV node. At higher rates, as in SVT's, the degree of block progresses to second because the atrial depolarization occurs during the relative refractory period of the ventricles. So at rest there is 1:1 conduction and at higher rates there are occasional "dropped beats" or 2:1 or 3:1 block or more.

Additionally, where a patient suffers from brady/tachy syndrome, the abnormal slowness of the pulse rate may be such that the stimulation of the heart muscles can be better controlled as with an implantable electronic pacemaker and, in such cases, it may be desirable to ablate the conduction pathways in conjunction with implanting such a pacemaker.

Ablation of a portion of ventricular tissue may be sufficient to prevent the occurrence of ventricular tachycardia. Elimination of abberent ventricular conduction pathways should prevent VT's.

Additionally, in conducting research for the development of pacemakers and other implantable pulse generators, it is necessary to experiment with animals. In such case, in conjunction with implanting an experimental pulse generator, it may be necessary to locate and ablate a cardiac conduction pathway.

The techniques employed in the prior art, such as described in the patent to Bures U.S. Pat. No. 3,865,118, have included the difficult operation of surgically sectioning the His Bundle to produce A-V block. Bures proposed that the SA node be destroyed so that the heart rate may drop abruptly without the necessity of destroying the His Bundle, during the implantation of a pacemaker. In either event, however, Bures contemplates opening the chest to have access to the heart muscle.

It is therefore desirable to provide apparatus and method for ablating the cardiac conduction pathways without the necessity of surgically opening the patient's chest to provide access to the heart muscle. Instead, it is desirable to provide means which may be nonsurgically inserted into the heart muscle to locate and ablate such pathways.

Catheters are known in the art and generally take the form off an elongated tubular element having at least one lumen extending throughout its length. These catheters have a distal end which is inserted into a cavity, artery or the like within a patient's body and a proximal end located externally of the patient's body. Such catheters are known wherein fiber optic means extend from the proximal end to the distal end so that a surgeon may deliver light to a cavity or the like and view the illuminated cavity by means located at the proximal end of the catheter. Additionally, some catheters also carry additional fiber optic means for transmitting a laser beam to the illuminated cavity for applying laser energy to the body tissue thereat. Such a catheter is disclosed, for example in the M. Bass U.S. Pat. No. 3,858,577. However, there is no suggestion in Bass that the catheter carries some means, such as electrodes or the like, responsive to electrical impulses transmitted by the cardiac conduction pathways for purposes of locating such pathways and also some means for ablating the thus located cardiac conduction pathways.

Catheters are known, however, which carry electrodes and such is illustrated in the A. R. Bures U.S. Pat. No. 3,865,118, supra. However, Bures employs the electrodes for purposes of stimulating heart muscles, including both atrial and ventricular stimulation. No suggestion is provided in Bures of employing electrodes for purposes of locating cardiac conduction pathways as well as some means for ablating the thus located pathways.

SUMMARY OF THE INVENTION

It is an object of the present invention to provide apparatus and method for locating and then ablating cardiac conduction pathways.

It is a still further object of the present invention to provide a catheter carrying means for locating and then ablating such cardiac conduction pathways.

It is a still further object to provide such a catheter which may be easily insertable into the heart chambers for locating elements of the cardiac conduction pathway including the SA node, the A-V node, the Bundle of His and areas of the V-A re-entry and the like.

In accordance with the invention, apparatus is provided for locating and ablating cardiac conduction pathway tissue within a heart employing an elongated catheter tube having a distal end adapted to be inserted through a passageway leading into a heart chamber proximate to a cardiac conduction pathway. The catheter carries conduction pathway locating means including at least one electrode means adapted to be located within the heart proximate to a conduction pathway for monitoring the level of electrical conduction at the site of interest. An ablation means is carried by the catheter for ablating at least a portion of the thus located cardiac conduction pathway tissue.

BRIEF DESCRIPTION OF THE DRAWINGS

The foregoing and other objects and advantages of the present invention will become more apparent from a consideration of the following description as taken in conjunction with the accompanying drawings, wherein.

DETAILED DESCRIPTION OF PREFERRED EMBODIMENT

Figure 1:
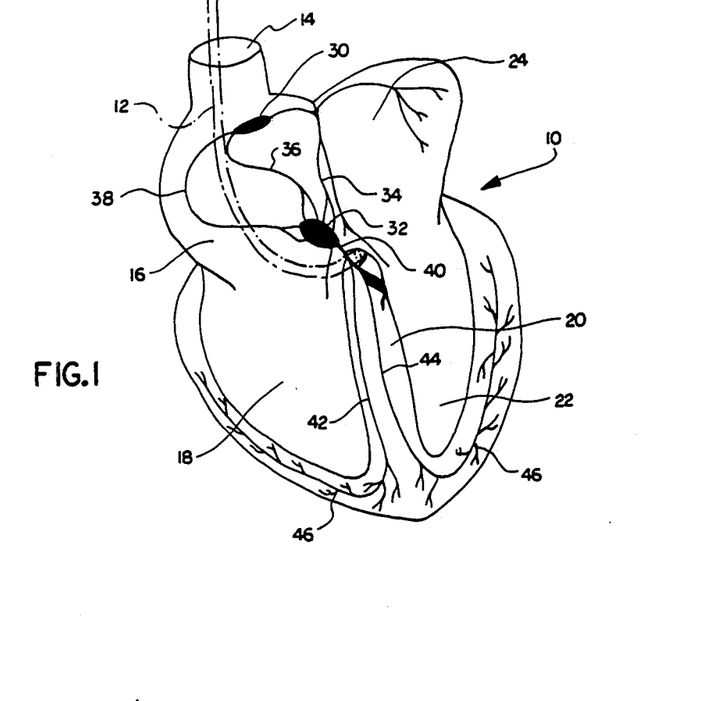
FIG. 1 is a schematic illustration of a heart having a catheter inserted therein for locating and ablating cardiac conduction pathways.

Reference is now made to the drawings which are for purposes of illustrating a preferred embodiment of the invention only, and not for purposes of limiting same. FIG. 1 is a schematic illustration of a heart 10 illustrating the anatomy of specific cardiac conduction pathways which, in accordance with the invention, are located and ablated by means of a catheter 12, to be described in greater detail hereinafter. In the schematic illustration of FIG. 1, the catheter 12 is shown as having entered the heart by way of the superior vena cava 14 and thence into the right atrium 16 in the area above the right ventricle 18. The cardiac conduction pathways are embedded within the walls of the heart, including a dividing septum wall 20 which separates the right ventricle 18 from the left ventricle 22. The left atrium 24 is located immediately above the left ventricle 22.

The cardiac conduction pathways to be discussed below are all embedded within the heart wall within muscular tissue and the like. For example, the sino-atrial node 30, hereinafter referred to as the S-A node, is embedded within muscular tissue in the wall of the right auricle or atrium 16. More specifically, the S-A node is located around the opening of the superior vena cava 14, in the right atrial myocardium. This is connected to the atrio-ventricular node 32, hereinafter referred to as the A-V node, by means of conductive pathways including a posterior internodal tract 34, a mid-internodal tract 36 and an anterior internodal tract 38. The A-V node is situated below the orifice of the coronary sinus in the atrial septum. The A-V node 32 transmits the impulses to sometimes referred to as the His Bundle 40, and thence by way of two branches known as the right bundle 42 and the left bundle 44 to the Purkinje fibers 46. The Purkinje fibers as illustrated in FIG. 1 are located in the myocardium of the ventricles 18 and 22.

The His Bundle 40 is situated below the medial leaflet of the tricuspid valve. The right bundle 42 is made of a long, thin fascicle which runs along the ventricular septum to branch out into the Purkinje fibers of the right ventricle. The left bundle 44 is formed by two fascicles, a long thin anterior fascicle and a short and thick posterior fascicle. Both fascicles branch out into the the left ventricular Purkinje fibers. The Purkinje fibers 46 are the last and finest ramification of the specific right and left bundles which propagate within the myocardium of the two ventricles.

The cardiac conduction pathways include automatic or pacemaker cells, such as the S-A node 30 and the A-V node 32. The pathways also include contractile cells, which do not have the ability to form spontaneous impulses while being excited. These include tracts 34, 36 and 38, the His Bundle 40, the right and left bundles 42 and 44 and the Purkinje fibers 46.

The cardiac muscle has a spontaneous and rythmic rate. It is the sequence of contraction which is of importance. Normally, the sino-atrial node has an inherently faster rate than does the atrial myocardium. The atrial rate is faster than the ventricular rate. The faster rate dominates so that the resulting rate is that of the sino-atrial node. If there is a block in the Bundle of His, one will see a faster atrial rate and a much slower ventricular rate. Usually, the ventricular contractions are not associated with atrial contractions. This disassociation can often result in a low cardiac output (this is one of the reasons patients with heart block faint—insuficient oxygenated blood to the brain) or the ventricles are inadequatey filled with blood from the atrium. Therefore, it is the orderly sequence of the atrial contractions filling the ventricles and then the ventricular contraction pumping blood into the pulmonary and systemic circulation that is of importance.

Figure 2:
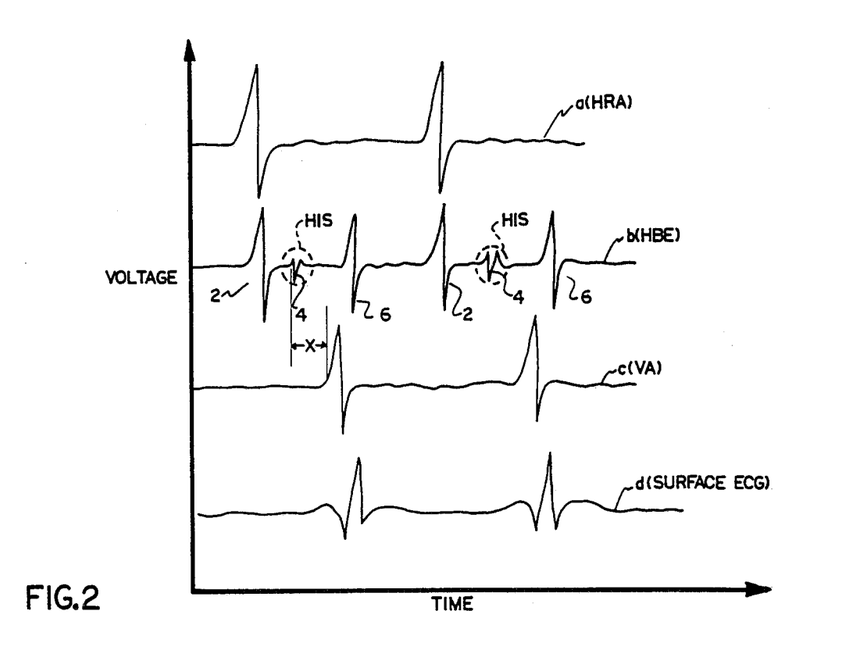
FIG. 2 is a graphical illustration showing curves a through d representing different heart activity potentials.

Reference is now made to curves a through d of FIG. 2 which are potentials with respect to time of different areas of the heart. Curves a, b and c, respectively represent the high right atrium (HRA), the His Bundle Electrogram (HBE), and the ventricular apex (VA) potentials. Curve d is representative of a surface measured electrocardiogram, sometimes referred to as an ECG curve. In curve b, the HBE shows in succession the atrial activity 2, the His Bundle activity 4 and the ventricular activity 6.

In accordance with the present invention, the catheter 12 is insertable into the chambers of the heart, such as into the right atrium 16 or into the right ventricle 18, so that the distal end of the catheter may be positioned against the heart walls in close proximity to one of the conduction pathways discussed above. The catheter, as will be described in greater detail hereinafter, carries means for electrically sensing the potentials illustrated in curves a–c of FIG. 2. These are monitored by means connected at the proximal end of the catheter. If, for example, the pathway of interest is the His Bundle 40, then the distal end carrying the electric potential sensing means is located proximate to the His Bundle and a potential corresponding with that of curve b in FIG. 2 is monitored by metering circuitry connected to the proximal end of the catheter. Assuming that it is desirable to ablate the conduction pathway at this location, a laser beam is directed from the distal end of the catheter to injure or ablate the tissue. The operator monitoring the meter may note some thermal enhancement of conduction time through the AV node, followed by asynchrony of the atria and ventricles, at which time lasing of the tissue is terminated. Suspension of lasing at the proper moment will result in 3°, 2°, 1° or no heart block.

The catheter 12 which carries the conduction pathway locating means as well as the pathway ablating means preferably takes the form of a torque controlled catheter such as that constructed in accordance with U.S. Pat. No. 3,585,707 to R. C. Stevens, the disclosure of which is herein incorporated by reference. Briefly, as described in that patent and shown herein at FIG. 3, the catheter 12 is an intravascular catheter having an elongated body portion 50 and a tip 52 at the distal end of the catheter. A lumen extends throughout the length of the catheter so that a fiber optic conduit or the like may be carried by the catheter. The body portion 50 of the catheter is reinforced so that it may be twisted at its proximal end to impart a twisting motion throughout its length. This body portion is constructed to have high longitudinal flexibility and high torsional control without being elastic. The body portion includes tubing made up of an inner plastic tubular core covered by a braided wire intermediate sheath and an outer plastic covering which penetrates through the interstices in the braiding of the sheath and closely overlies the tubular core. The tip portion 52 is designed to direct the catheter during insertion into a selected vessel and is formed with a taper having a pair of curves including a relatively sharp curve on the order of 45° just before the distal end thereof and a less sharp curve 56 a short distance proximally thereof. The curve tip does not employ a braided sheath as it is preferably more flexible than the body portion. As is seen in FIG. 1, the curve 54 near the distal end of the catheter permits ease in locating the distal tip adjacent to a portion of the cardiac conduction pathways, such as at the Bundle of His 40.

In each of the embodiments to be described hereinafter, a torque catheter as described above with respect to FIG. 3 is employed. It is contemplated that the distal end of the catheter will be inserted into a vessel of a patient leading to the interior of the patient's heart, such as in either the atrium chamber or the ventricular chamber. The flexible distal tip 52 will be positioned so that the distal end thereof will be proximate to a cardiac conduction pathway. The distal end of the catheter carries electrode means, which when positioned proximate to the cardiac conduction pathway will sense the signal conduction level or membrane potential of an excitable cell (pacemaker cell). The electrode means is electrically connected by suitable electrical connection means extending through the lumen of the catheter and thence beyond the proximal end thereof to a suitable monitor meter at which a surgeon may view the potential appearing, for example as one of the potentials illustrated in curves a–c in FIG. 2. The tissue of interest may be ablated by laser radiation and the laser source is turned off once the surgeon notes that his external monitor indicates the properly modified activity at the site of interest.

Figures 3, 4:
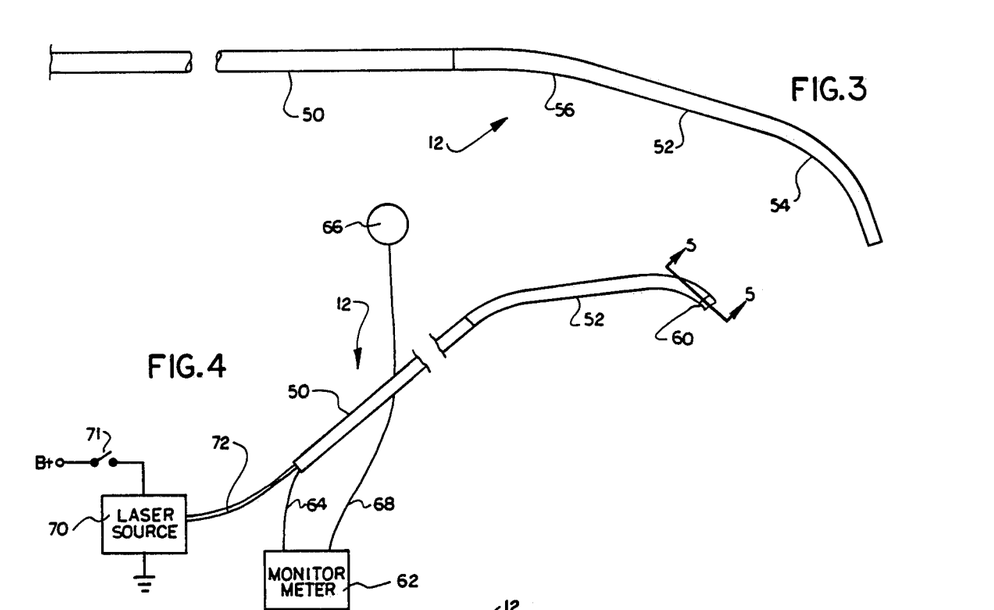
FIG. 3 is a schematic illustration of a torque controlled catheter which may be employed herein.
FIG. 4 is a schematic-block diagram illustration of one embodiment of the invention.
Figure 5:
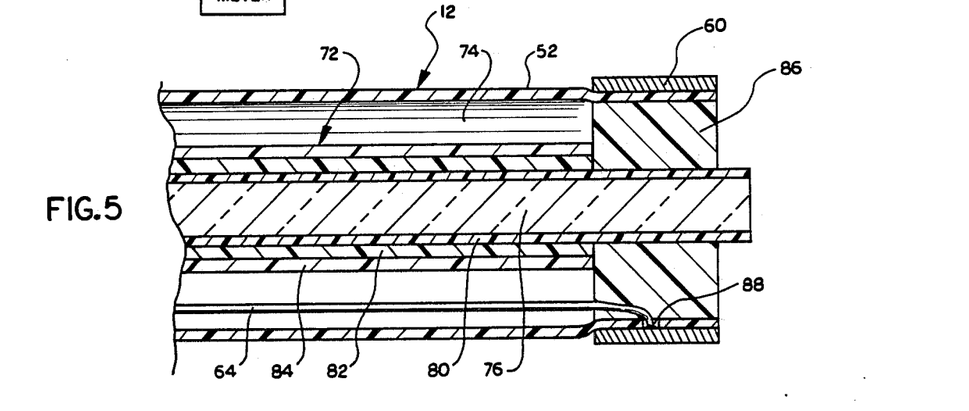
FIG. 5 is an enlarged sectional view of the distal end of the catheter in FIG. 4.

Turning now to FIGS. 4 and 5, there is illustrated one embodiment of the invention and which includes a torque controlled catheter 12 constructed in accordance with that discussed above with reference to FIG. 3 having an elongated body portion 50 and a tip portion 52. The tip portion is not reinforced and has at least one bend as to assist in locating a conduction pathway of interest within a heart chamber. At the distal tip, the catheter carries a stainless steel ring electrode 60. This is electrically connected to a suitable monitor meter 62 as by insulated conductor 64 which extends through the catheter's lumen. A second electrode 66 is adapted to be positioned on the exterior of the patient's body, such as on the chest immediately over the heart and preferably over the superior vena cava. This electrode 66 is connected by an external insulated conductor 68 to the monitor meter 62. The monitor meter 62 may take the form of a strip chart recorder or an oscilloscope or the like so that a surgeon may visually monitor the electric potential, which depending upon the region of interest will vary in a manner similar to that of curves a–c in FIG. 2. For ablation purposes, the surgeon will activate an located laser source 70 which supplies laser radiation to the site of interest by way of an optical fiber 72 which enters the proximal end of the catheter 12 and extends throughout its length and protrudes slightly beyond the distal tip of the catheter, as is best shown in FIG. 5.

With the use of an external electrode 66, the catheter of FIG. 4 provides unipolar sensing of the membrane's potential in the cardiac conduction pathway of interest. The laser source 70 may take various forms well known in the art. For purposes of ablating conduction pathway tissue, it has been found that a relatively low power laser source may be used, such as an argon laser source, which may provide relatively low energy laser radiation pulses.

Reference is now made to FIG. 5 which provides an exploded sectional view of the catheter at its distal tip and is taken generally along line 5—5 in FIG. 4 looking in the direction of the arrows. Here it is seen that the tip portion 52 is a tubular body of plastic material, preferably of polyurethane material and encases a single lumen 74. The catheter carries the optical fiber 72 within this lumen. Preferably, the optical fiber takes the form of a cladded single optical fiber. This fiber has a core 76 which may take the form of a 200 micra thick silica core. This is covered by a cladding 80 which may be of a thickness on the order of 25 micra and constructed of silica material. The cladding 80 is, in turn, encased by a sleeve 82 which may be on the order of 50 micra in thickness and constructed of a silicon polymer. The sleeve 82, in turn, is surrounded by a jacket 84 which may be on the order of 50 micra in thickness and may be constructed of Tefzel material or the like.

The jacket 84 and the sleeve 82 have been stripped away from the optical fiber for a short portion of its length adjacent the distal end where the fiber extends through the electrode ring 60. It is to be noted that the optical fiber protrudes slightly beyond the electrode ring on the order of about 1 milimeter. The annular spacing between this extended portion of the optical fiber and the surrounding inner wall of catheter 12 and ring 60 may be filled, as with a suitable epoxy 86, so as to hold the optical fiber in place. The epoxy 86 is chosen such that its degradation temperature is greater than the temperature generated. Alternatively, the operating temperature of the laser is chosen such that the temperature and rise time is less than the degradation temperatures of the epoxy. Sapphire may be substituted for the epoxy 86. The insulated conductor 64 also extends through the lumen 74 and is soldered or otherwise spot welded at 88 to the inner surface of the electrode ring 60 so as to make good electrical contact therewith. The proximal end of the conductor 64 exits from the catheter and is intended to be electrically connected to a meter, such as monitor meter 62 (FIG. 4).

In operation, the catheter 12 has its distal end inserted into a patient's vessel, such as peripheral vein, and is advanced as by way of the superior vena cava into the right atrium of the heart (see FIG. 1). The external reference electrode is placed on the patient's chest, preferably in the area over the superior vena cava. The recording electrode 60 at the distal tip of the catheter is advanced to a selected site at which the potential of a specific cardiac conduction pathway is to be monitored. This site, for example, may correspond with the Bundle of His 40 (FIG. 1). With the recording electrode 60 in place proximate to the Bundle of His 40, a surgeon may observe the monitor meter 62 and note that the potential between electrodes 60 and 66 appears similar to that of curve d in FIG. 2. Notice that the potential for each pathway has a characteristic waveform. When ablation of the His Bundle is desired, a surgeon may activate the laser source 70, as by closing a switch 71, connecting the laser source with a suitable source of energy such as a B+ voltage supply source. The catheter may be pulled back slightly as the laser source is energized with the radiation being then fired from the distal tip of the optical fiber 72. Disruption of the conduction pathway at the site of application may be achieved by using low energy pulses from the laser source. Complete disruption (ablation) of the pathway has occurred when the surgeon notes that the atrial and ventricular activity have become asynchronous.

The same procedure as stated above may be followed with respect to locating and ablating other areas of the cardiac conduction pathway. Depending upon which site is of interest, the distal tip 52 may need to be bent slightly different than that of another site. However, in using this technique, anomalous conduction pathways and ectopic foci can be located by monitoring the membrane's potential on the monitor meter 62 and then ablating the tissue in the same manner as discussed above. If desired, the distal end may be modified to include a port through which saline solution can be used for flushing purposes. The ring electrode 60 can either be attached to the end of the catheter tube or applied over the tube by a press fit in the manner illustrated in FIG. 5. Whereas the catheter body has been described as being fabricated of a polyurethane material, it may be fabricated of other suitable plastic materials permitting a preform curve and curve retention for positioning the catheter in the required location.

Figure 6:
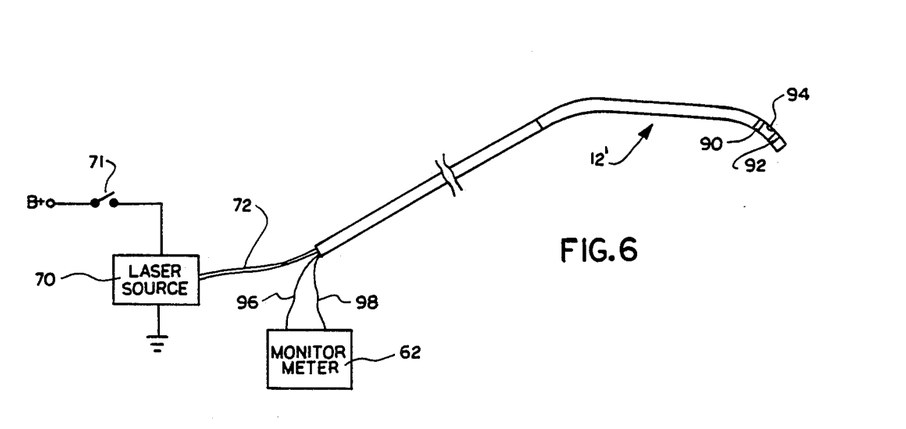
FIG. 6 is a schematic-block diagram illustration of a second embodiment of the invention.
Figure 7:
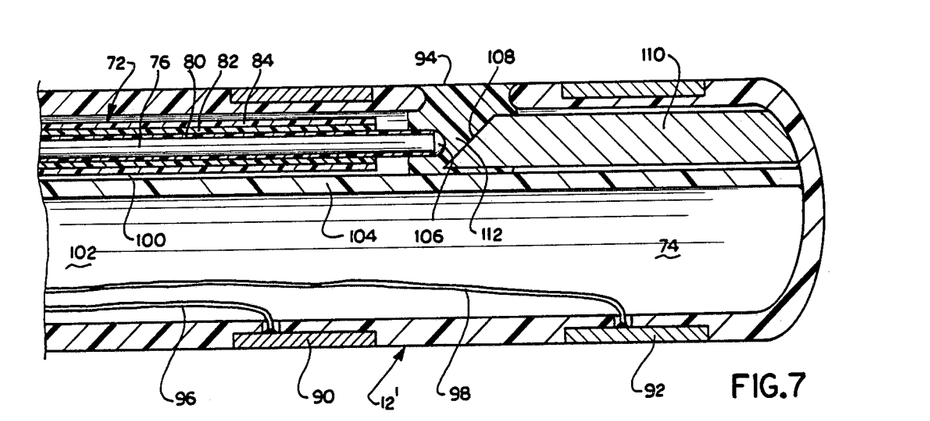
FIG. 7 is an enlarged sectional view of the distal end of the catheter in FIG. 6.

Reference is now made to FIGS. 6 and 7 which illustrate a second embodiment of the invention for bipolar sensing of the potentials at different locations of the cardiac conduction pathway. As illustrated in FIG. 6, this embodiment is quite similar to that as illustrated in FIG. 4, and consequently like reference numerals will be employed for identifying like components and only the differences of the two embodiments will be described herein in detail.

As shown in FIG. 6, catheter 12' is constructed essentially the same as that of FIG. 4 with the exception that its distal end is closed and just prior to the distal end there is provided a pair of longitudinally spaced ring electrodes 90 and 92 straddling a window aperture 94 which serves as a side port through which laser radiation may be emitted for lasing tissue at a site of interest. As best seen in FIG. 7, a pair of insulated conductors 96 and 98 each have one end soldered or otherwise electrically secured to the inner surface of electrodes 90 and 92, respectively. In this embodiment, the catheter 12' has two lumens 100 and 102 separated by a wall 104. The electrical conductors 96 and 98 are located in lumen 102 and extend from the electrodes 90 and 92 throughout the length of the catheter and exit from the proximal end thereof and are suitably connected to a monitor meter 62 for recording and/or displaying the electrical potentials existing between the electrodes.

An optical fiber 72, constructed in the same manner as that discussed with reference to FIG. 5, extends from a laser source 70 into the proximal end of the catheter and then is carried within lumen 100 to the area of the electrodes 90 and 92. As in the case of FIG. 5, a portion of the length of sleeve 82 and jacket 84 has been stripped away at the distal end of the optical fiber, as is seen in FIG. 7. This prevents burning of these components by the argon laser radiation. A microlens 106 has been provided at the distal tip of the optical fiber and this is accomplished by fire polishing the tip of the silica core 76. Spaced downstream from lens 106 there is provided a stainless steel, polished mirror 108 angled at approximately 45 degrees so as to deflect radiation from the optical fiber transversely through window 94 for side port lasing of tissue. The mirror 108 is conveniently provided by polishing a 45 degree angle at one end of a stainless steel rod 110 also located in lumen 100 at the distal end of the catheter but could also be a polished curved surface. The aperture or window 94 in the catheter provides a cavity within the lumen 100 between the optical fiber and mirror 108. This cavity is filled with a transparent epoxy 112, such as Epo-Tek or Tracon Bipax to prevent blood from contaminating the optical fiber or the mirror 108. Epoxy 112 is preferably chosen such that its degradation temperature is greater than the temperature generated by the heat it absorbs at the wavelengths of the laser. Alternatively, the on time of the laser is chosen so that the temperature is less than the degradation temperature of the epoxy. The epoxy 112 may be replaced with sapphire.

In operation, the conduction ablation catheter of FIGS. 6 and 7 is employed in the same manner as that discussed previously with reference to FIGS. 4 and 5. However, since bipolar sensing is being accomplished, it is preferred that the distal end of the catheter be positioned so that the electrodes 90 and 92 somewhat straddle the tissue containing a conduction pathway. A surgeon may then note the membrane potential, such as that for a His Bundle as indicated by curve b in FIG. 2, and if ablation is desired, he will then actuate the laser source 70 by closing switch 71. The laser radiation will be reflected by mirror 104 and exit through the side port window 94 for lasing the tissue at the site. The lasing may continue by low energy pulses until the surgeon notes from the monitor meter that complete atrio-ventricular dissociation has occurred.

In the embodiment of FIGS. 6 and 7 just described, the electrodes 90 and 92 are preferably ring electrodes which may be embedded in the outer wall of the catheter or may be applied, as with a press fit. Each has a width, as viewed along the length of the catheter, on the order of 2 millimeters and the window or aperture 94 in the catheter wall may also have a width on the order of approximately 2 millimeters. The electrodes need not be ring electrodes coaxially surrounding the catheter, as is illustrated in FIG. 7, but may be replaced as with small stainless steel plates, each on the order of about 2 millimeters in diameter and spaced apart as discussed above. Although two lumens are illustrated in FIG. 7, the catheter may also be constructed with but a single lumen. It is not essential that the tip of the catheter be closed, as is illustrated in FIG. 6, but may be open. However, the cavity area between lens 106 and mirror 108 is preferably filled with a transparent epoxy to prevent contamination by blood. Also, the mirrored stainless steel rod 110 can be fused into the nonreinforced polyurethane tip 52 during the construction, prior to joining the tip to the body portion 50.

Figure 8:
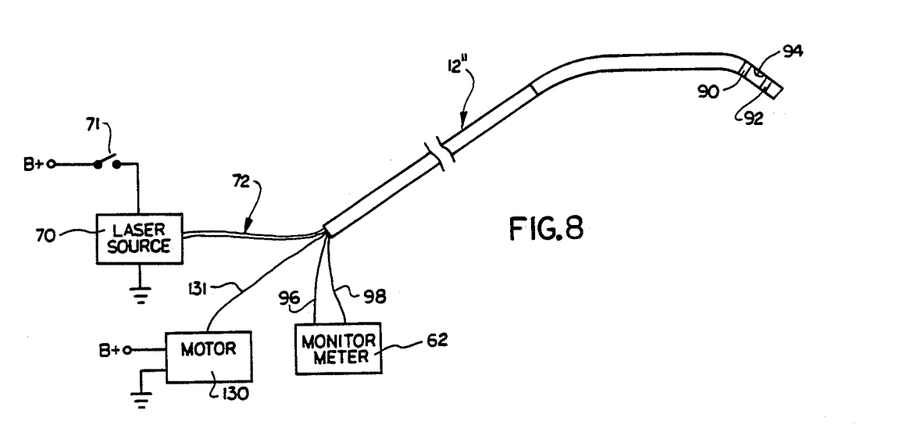
FIG. 8 is a schematic-block diagram illustration of a third embodiment of the invention; and, FIG. 9 is an enlarged sectional view of the distal end of the catheter in FIG. 8.
Figure 9:
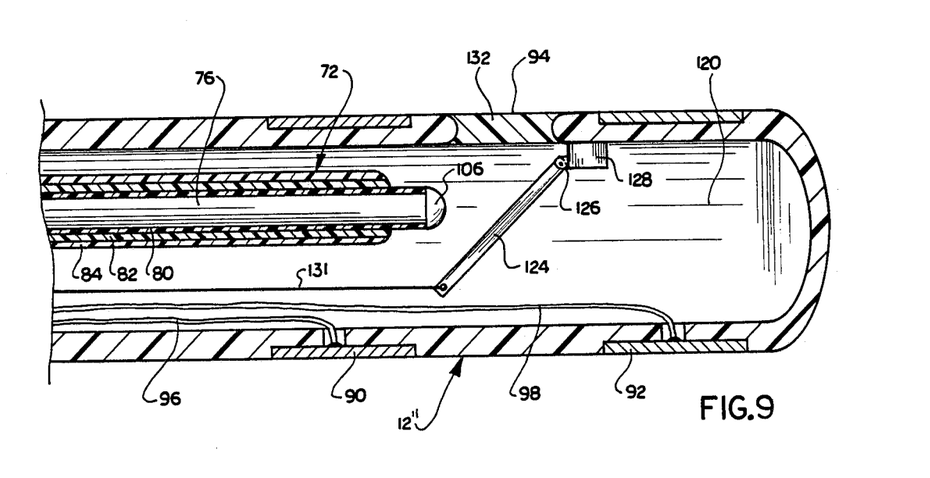

Reference is now made to FIGS. 8 and 9 which illustrate a third embodiment of the invention which is quite similar to that in FIGS. 6 and 7 and like components will be described with like character references. The catheter 12" is quite similar to that in FIG. 6 except that it includes but a single lumen 120 which houses optical fiber 72. The optical fiber is constructed in the same manner as that as discussed with reference to FIG. 7 and includes a polished lens 106. This catheter also includes a pair of spaced apart ring electrodes 90 and 92 having insulated conductors 96 and 98 connected thereto and extending through the single lumen 120 to the proximal end of the catheter and, thence, to a monitor meter 62. The optical fiber 72 extends through the single lumen of the catheter 12" and exits from the proximal end where it connects with the laser source 70 in the same manner as discussed hereinbefore.

The main difference in this embodiment is the provision of a pivotal mirror 124 which replaces the fixed mirror 108 of the embodiment in FIG. 7. The pivotal mirror 124 is a polished stainless steel mirror which is pivotally mounted to a suitable pivot post 126 extending from a strut 128 secured to and depending from the inner surface of the catheter 12". Pivotal motion is accomplished by a steel wire 131 (which may be insulated) and which is secured to the bottom end of the mirror. The steel wire extends through the lumen of the catheter and exits from the proximal end thereof where force may be applied to the wire, causing the mirror to pivot about the pivot post. This will vary the angle of reflection of laser radiation which strikes the mirror so as to exit through the side port window 94. Preferably, the proximal end of wire 131, as it exits from the catheter, is connected to a suitable motor 130 having controls for driving the wire in a forward or reverse direction, as desired, to adjust the mirror's reflection angle. A support fixture, not shown, may be located within the catheter near its proximal end and having two lumens or apertures, one for supporting the optical fiber 72 and the other for supporting or guiding conductors 96, 98 and the steel wire 131.

In this embodiment, the catheter is closed at its distal end and preferably the window 94 is sealed as with a transparent epoxy 132 so as to permit the passage of laser radition while preventing contamination of the mirror and lens 106 as by blood and the like. Epoxy 132 is chosen as in the case of epoxy 112, discussed above, or may be replaced by sapphire.

The operation of the embodiment of FIGS. 8 and 9 is similar to that discussed with reference to FIGS. 6 and 7 but offers additional features. After the operator has located a conduction pathway, such as a bundle of His, as discussed hereinbefore, he may activate the laser source 70 and apply low level radiation, such as on the order of 10 joules. The potential, as measured across electrodes 90 and 92, is displayed at the monitor meter 62. If the conduction pathway at the site is injured but not totally ablated and then allowed to stabilize, then the time interval between the activity in the atrium and that at the bundle of His should increase. For example, the time interval may be visualized with respect to FIG. 2 as being the time interval X between points on curve b. If the patient has a cardiac arrythmia indicating an abnormal rapidity of heart action, tachycardia, then an increase in the time interval X could well be indicative of a longer conduction time through the AV node; sufficiently long so that partial heart block improves the health of the patient. In other words, during an atrial tacycardia, not all of the atrial beats would be conducted to the ventricles. Therefore, despite the excessive rapidity of the atrial activity, and associated failure to pump blood, the ventricles would continue to pump at a slower and safer rate. However, if it is desired to totally ablate the conduction pathway, then the operator may increase the energy level of the argon laser radiation and destroy the conduction pathway.

On the other hand, if the time interval X does not increase after radiating the tissue at the site of interest, this may be indicative that the angle of the mirror should be changed. In this embodiment, the operator may now activate motor 130 to change the angle of the mirror, as desired, and then again activate the laser, first at a low energy level and determine whether or not the timing interval X decreases due to thermal enhancement of AV nodal automaticity. Alternatively, the mirror may be swept back and forth continuously until the operator notes a decrease in the time interval X. If it is desired to totally ablate the conduction pathway, the operator will increase the radiation level sufficient to destroy the conduction pathway. Modification can be made by providing a closed loop system wherein feedback from conductors 96 and 98 may be transmitted to a control circuit for operating the motor 130 and also the laser source 70 so as to coordinate the mirror sweep time to a particular time interval of for example, 2 seconds, and then automatically control the level of radiation emitted by the laser source in dependence upon a predetermined variation in the time interval X.

Although the invention has been described in conjunction with preferred embodiments, it is to be appreciated that various modifications may be made without departing from the spirit and scope of the invention as defined by the appended claims.

Having described specific preferred embodiments of the invention, the following is claimed:

1. Apparatus for locating and ablating cardiac conduction pathway tissue within a heart, comprising:
   an elongated catheter tube having a proximal end and a distal end, said distal end adapted to be inserted into a passageway and advanced therethrough into a heart chamber proximate to a cardiac conduction pathway in the heart wall,
   conduction pathway locating means carried adjacent the distal end of said catheter tube and including at least one electrode means for being positioned proximate to a conduction pathway for electrically sensing the membrane potential at that site, and
   conduction pathway ablation means independent of said locating means and carried by said catheter tube adjacent the distal end thereof for ablating at least a portion of the conduction pathway at the located site.

2. Apparatus for locating and ablating cardiac conduction pathway tissue within a heart, comprising:
   an elongated catheter tube having a proximal end and a distal end, said distal end adapted to be inserted into a passageway and advanced therethrough into a heart chamber proximate to a cardiac conduction pathway in the heart wall,
   conduction pathway locating means carried adjacent the distal end of said catheter tube and including at least one electrode means for being positioned proximate to a conduction pathway for electrically sensing the membrane potential at that site, and
   conduction pathway ablation means carried by said catheter tube adjacent the distal end thereof for ablating at least a portion of the conduction pathway at the located site, said ablation means includes means for transmitting laser radiation to said site for ablating the conduction pathway thereat.

3. Apparatus as set forth in claim 2 wherein said means for transmitting laser radiation includes elongated fiber optic means located within said elongated catheter tube and extending essentially throughout the length of said catheter tube.

4. Apparatus as set forth in claim 3 wherein said fiber optic means has a distal end located adjacent the distal end of said catheter tube and a proximal end which exits from said catheter tube and is adapted to be connected to a source of laser radiation so that laser radiation may be transmitted by way of said fiber optic means to exit from the distal end thereof.

5. Apparatus as set forth in claim 4 wherein said fiber optic means is mounted so that radiation is directed axially of the distal end of said catheter tube.

6. Apparatus as set forth in claim 5 wherein the distal end of said fiber optic means extends slightly beyond that of said catheter tube so as to direct radiation axially from the distal end thereof.

7. Apparatus as set forth in claim 4 wherein the distal end of said fiber optic means terminates short of the distal end of said catheter tube, said catheter tube having a window aperture in its side walls short of the distal end thereof and in alignment with the distal end of said fiber optic means for directing radiation therefrom transversely of the axis of said catheter tube.

8. Apparatus as set forth in claim 7 including mirror means mounted within said catheter tube downstream from the distal end of said fiber optic means and arranged to reflect laser radiation emitted from said fiber optic means transversely through said window aperture.

9. Apparatus as set forth in claim 8 wherein said mirror means is aligned to provide a reflecting surface inclined by an angle of 45 degrees with respect to the optical axis of said fiber optic means.

10. Apparatus as set forth in claim 8 wherein said mirror means is pivotally mounted to said catheter tube so as to adjust the angle of reflection of said laser radiation.

11. Apparatus as set forth in claim 10 including means connected to said mirror for adjusting said angle wherein said adjusting means extends from said mirror means through said catheter tube to said proximal end thereof.

12. Apparatus as set forth in claim 11 wherein said adjusting means includes a wire member having a distal end and a proximal end and having its proximal end exiting from the proximal end of said catheter tube so that said wire member may be moved inwardly and outwardly to adjust the reflection angle of said mirror means.

13. Apparatus as set forth in claim 12 including motor means in engagement with the proximal end of said wire member for imparting driving forces to said wire member.

14. Apparatus as set forth in claim 4 wherein said at least one electrode means includes an electrically conductive member mounted on the exterior surface of said catheter tube proximate to the distal end thereof.

15. Apparatus as set forth in claim 14 wherein said electrode means is a single electrically conductive member taking the form of an annular ring.

16. Apparatus as set forth in claim 15 including conductive means electrically connected to said ring and extending within said catheter tube and exiting from the proximal end thereof for connection with electrical signal measuring means.

17. Apparatus as set forth in claim 16 wherein said fiber optic means extends beyond the distal end of said catheter tube and said ring electrode means coaxially surrounds said fiber optic means and said fiber optic means transmits radiation in a direction axially of the optical axis thereof.

18. Apparatus as set forth in claim 4 wherein said at least one electrode means includes a first electrode means and a second electrode means carried on the exterior surface of said catheter tube proximate to the distal end thereof and wherein said first and second electrode means are longitudinally spaced from each other and serve to provide bipolar sensing of the membrane potentials at a site of interest within the heart.

19. Apparatus as set forth in claim 19 wherein said first and second electrode means each comprises an annular ring coaxially surrounding said catheter tube.

20. Apparatus as set forth in claim 18 wherein said catheter tube has an aperture formed therein intermediate said first and second electrode means for defining a side port for emitting radiation transversely of the catheter tube.

21. Apparatus as set forth in claim 20 wherein the distal end of said fiber optic means terminates within said catheter tube proximate said aperture so that laser radiation emitted thereby may be directed through said aperture in a direction transversely of said catheter tube.

22. Apparatus as set forth in claim 21 including mirror means mounted within said tube and positioned downstream from the distal end of said fiber optic means for reflecting laser radiation through said aperture.

23. Apparatus as set forth in claim 22 wherein the distal end of said fiber optic means is provided with a lens structure for directing the laser radiation therefrom.

24. Apparatus as set forth in claim 22 wherein said mirror means is pivotally mounted within said catheter tube so as to be pivotally adjusted to vary the angle of reflection for directing said laser radiation.

* * * * *